United States Patent
Morales et al.

(10) Patent No.: US 6,361,533 B1
(45) Date of Patent: Mar. 26, 2002

(54) SURGICAL TUBULAR-SHAFTED INSTRUMENT

(75) Inventors: Pedro Morales; Markus Nesper, both of Tuttlingen; Dieter Weisshaupt, Immendingen, all of (DE)

(73) Assignee: Aesculap AG & Co. KG, Tuttlingen (DE)

( * ) Notice: Subject to any disclaimer, the term of this patent is extended or adjusted under 35 U.S.C. 154(b) by 0 days.

(21) Appl. No.: 09/521,147

(22) Filed: Mar. 8, 2000

Related U.S. Application Data

(63) Continuation of application No. PCT/EP98/05805, filed on Sep. 11, 1998.

(30) Foreign Application Priority Data

Sep. 18, 1997 (DE) .......................................... 197 41 054

(51) Int. Cl.⁷ ................................................ A61B 18/18
(52) U.S. Cl. .......................................... 606/45; 606/49
(58) Field of Search ................................. 606/205, 170, 606/45–52; 600/564; 401/6–8

(56) References Cited

U.S. PATENT DOCUMENTS

| | | | | |
|---|---|---|---|---|
| 5,275,612 A | * | 1/1994 | Bales, Jr. ..................... | 606/205 |
| 5,370,659 A | * | 12/1994 | Sakashita ..................... | 606/205 |
| D378,601 S | * | 3/1997 | Sakuno ......................... | D19/48 |
| 5,618,308 A | * | 4/1997 | Holmes et al. .............. | 606/205 |
| 5,722,988 A | | 3/1998 | Weisshaupt | |
| 5,766,167 A | * | 6/1998 | Eggers et al. ................. | 606/46 |
| 5,843,122 A | * | 12/1998 | Riza ............................ | 600/564 |
| 5,947,996 A | * | 9/1999 | Logeman ..................... | 606/205 |
| 5,988,908 A | * | 11/1999 | Kageyama et al. ........... | 401/6 |
| 6,063,086 A | * | 5/2000 | Benecke et al. .............. | 606/51 |

FOREIGN PATENT DOCUMENTS

| | | |
|---|---|---|
| DE | 32 17 105 | 11/1983 |
| DE | 41 13 037 | 10/1992 |
| DE | 93 18 815.3 | 3/1994 |
| EP | 0 479 482 | 4/1992 |

\* cited by examiner

*Primary Examiner*—Kennedy Schaetzle
*Assistant Examiner*—Kristen L. Droesch
(74) *Attorney, Agent, or Firm*—Barry R. Lipsitz

(57) ABSTRACT

In order to make an improved securing of the plastic sheath on the holder possible in a surgical tubular-shafted instrument with a shaft, at the distal end of which at least one tool is arranged on a holder which, for its part, is secured in position on the shaft, and with a plastic sheath partially covering the holder, it is suggested that the plastic sheath engage at its edge beneath projections on the holder.

9 Claims, 3 Drawing Sheets

SURGICAL TUBULAR-SHAFTED INSTRUMENT

This application is a continuation of PCT/EP98/05805 filed Sept. 11, 1998.

BACKGROUND OF THE INVENTION

The invention relates to a surgical, tubular-shafted instrument with a shaft, at the distal end of which at least one tool is arranged on a holder which, for its part, is secured in position on the shaft, and with a plastic sheath partially covering the holder.

A tubular-shafted instrument of this type is known, for example, from DE 93 18 815 U1. It is possible with such a tubular-shafted instrument, on the one hand, to use very solid metallic materials for the construction of the holder and the shaft and, on the other hand, to electrically insulate the shaft, including the holder, towards the outside as far as the area of the tools, on the one hand by surrounding the shaft itself with an electrically insulating sleeve, on the other hand by the holder having in certain areas a plastic sheath which covers outwardly pointing areas of the metallic holder. If such a tubular-shafted instrument is used as an electrical cutting and coagulation instrument, it is ensured in this way that any voltage applied to the instrument comes into contact with the body tissue only in the area of the actual tool so that cutting or coagulating occurs only in this area.

In practice, it has been shown that plastic sheaths of this type lift away from the holder in their edge area during the course of time and in this area cavities are formed which can become soiled and are very difficult to clean. This is due, on the one hand, to the fact that the material of the plastic sheath, which is normally applied by way of spraying on, does not combine with the material of the holder; this material may, for example, be high-quality steel. On the other hand, during the sterilization of these tubular-shafted instruments steam possibly penetrates the gap between the plastic sheath and the holder under increased pressure and increases the size of this gap so that the plastic material of the plastic sheath is removed from its areal contact on the holder.

The object of the invention is to design a generic tubular-shafted instrument such that such a lifting of the plastic sheath away from the holder and, in particular, the formation of larger cavities which are difficult to clean are avoided.

SUMMARY OF THE INVENTION

This object is accomplished in accordance with the invention, in a surgical tubular-shafted instrument of the type described at the outset, in that the plastic sheath engages at its edge beneath projections on the holder. The connection between the plastic sheath, on the one hand, and the holder, on the other hand, is thus designed such that the holder engages over the adjacent plastic sheath in the edge region and thereby prevents any lifting away from the supporting surface of the holder; in this way, a positive securing in position of the plastic sheath is, in practice, obtained in the edge region.

In a preferred embodiment it is provided for the projections to be formed by undercuts of a step in the holder which limits a lower-lying area of the holder covered by the plastic sheath. Such a step may, for example, extend over the entire circumference of the holder and results in the plastic sheath being secured in position on the holder in the same way along its entire edge.

In this respect, it is advantageous when the backwardly tapering cavity of the undercut is completely filled by the material of the plastic sheath. This results in a complete positive connection and prevents cavities, which can become soiled, being formed at any point.

It is particularly advantageous when the undercut is formed by a boundary surface of the step extending at an angle to the height of the step.

In accordance with a preferred embodiment, it is provided for the plastic sheath to adjoin non-sheathed, adjacent areas of the holder in a stepless manner so that a continuous outer surface is obtained which extends uniformly over the gap between holder surface and plastic sheath surface.

The material of the plastic sheath will preferably be a plastic material which can be sterilized by steam, for example, polyether ether ketone (PEEK) or liquid crystal polymer (LCP).

The following description of preferred embodiments of the invention serves to explain the invention in greater detail in conjunction with the drawings.

DETAILED DESCRIPTION OF THE INVENTION

Figure 1:
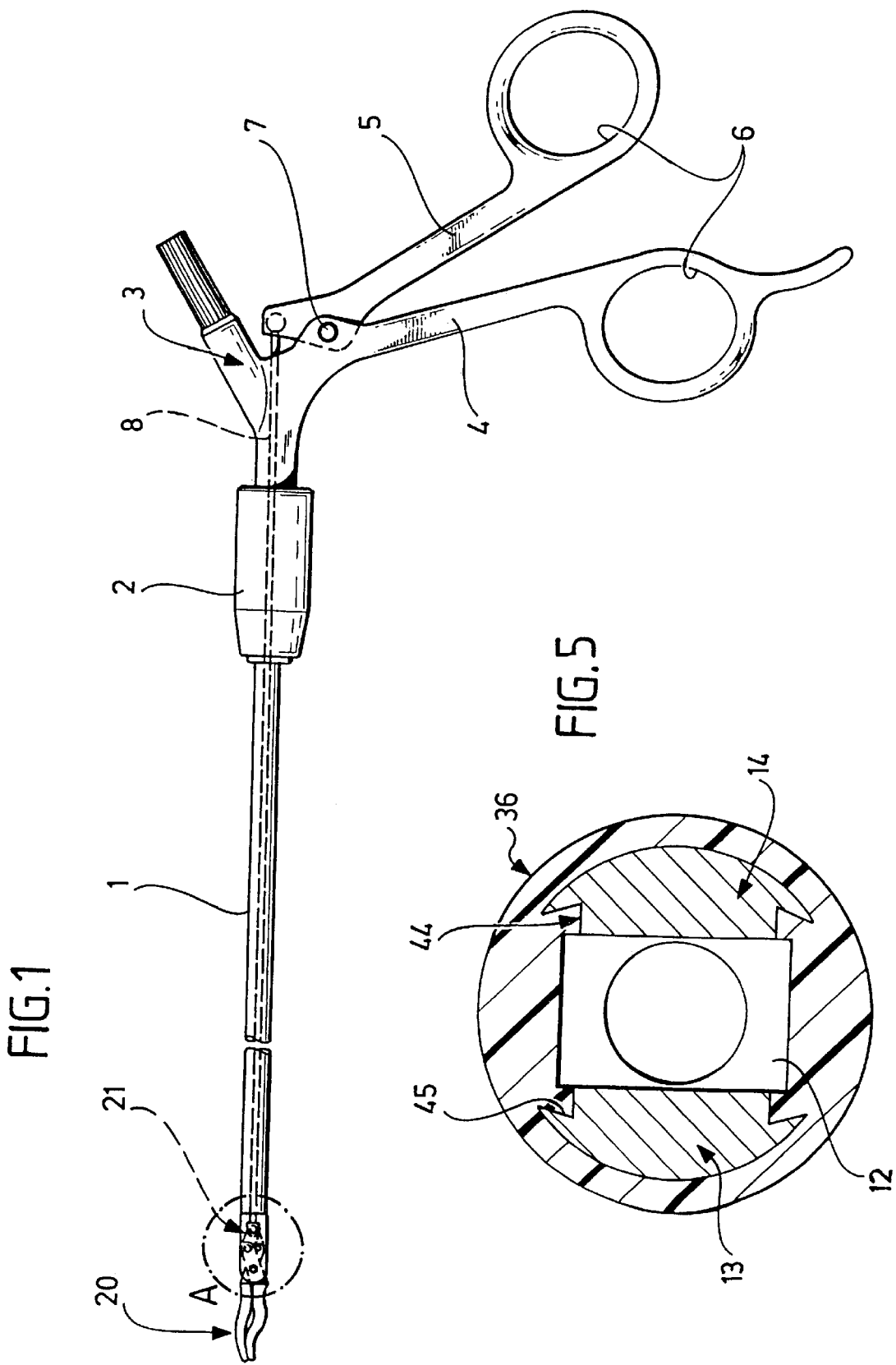
FIG. 1 a side view of a tubular-shafted instrument.
Figure 2:
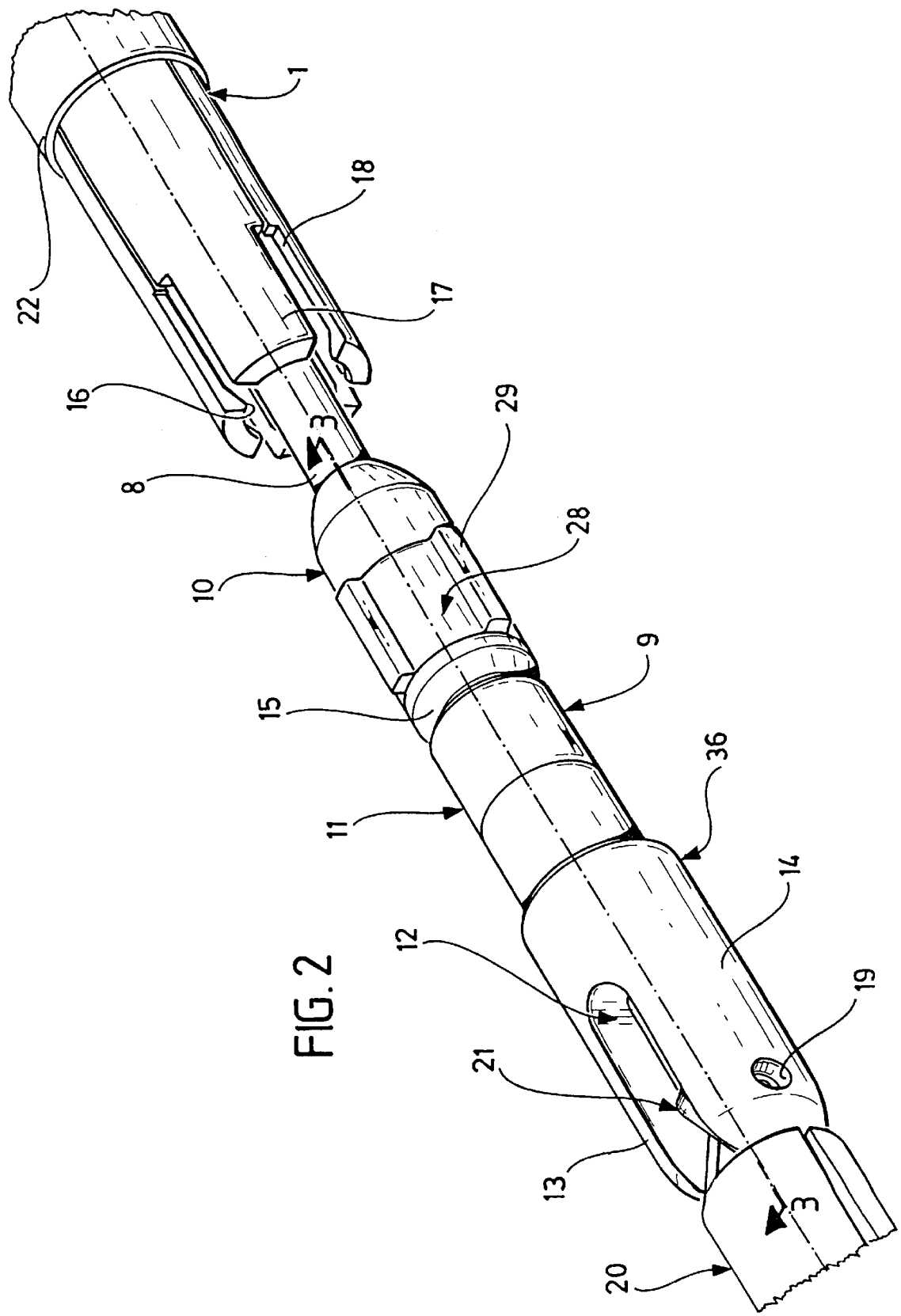
FIG. 2 a perspective partial view of the area A in FIG. 1 in a tubular-shafted instrument extended in longitudinal direction.

The tubular-shafted instrument illustrated in the drawings comprises a tubular shaft 1 which is detachably connected via a coupling member 2 to a handle part 3 at its proximal end. The handle part 3 has two branches 4, 5 with finger openings 6 which can be pivoted relative to one another about a pivot axis 7. The one branch 4 is connected to the shaft 1, the other branch 5 is articulatedly connected to a rod-shaped actuating element 8 which is arranged in the interior of the shaft 1 and extends as far as its distal end. During the pivoting of the branches 4 and 5 relative to one another, the actuating element 8 is displaced in longitudinal direction in relation to the shaft 1.

At the distal end, a tubular holder 9 engages in the shaft 1 and this holder has at its end facing the shaft 1 an insertion nipple 10, a cylindrical section 11 adjoining thereto and two longitudinal arms 13 and 14 adjoining thereto, these arms extending parallel to one another and forming a receiving space 12 between them.

The insertion nipple 10 can be inserted into the distal end of the shaft 1; at its area of transition to the cylindrical section 11 it has a circumferential groove 15, into which the inwardly projecting ends 16 of the wall sections 17 of the shaft 1 can dip. These wall sections 17 are subdivided by longitudinal cuts 18 into areas which are independent of one another so that these wall sections 17 form spring tongues which can be bent inwards or outwards and which are integrally connected to the shaft 1 consisting of a corresponding elastic material.

In the vicinity of their free end the longitudinal arms 13 and 14 have openings 19 which extend transversely to the longitudinal direction of the holder 9 and into which a bearing shaft of tools 20, which is not illustrated in the drawings, can be inserted so that the tools 20 are held in the receiving space 12 so as to be pivotable about the axis formed by the bearing shaft and protrude in a distal direction out of this space. These tools can, for example, be scissor blades, clamping jaws or the like. These tools 20 are pivoted via gear means 21 via the actuating element 8 when this is displaced in longitudinal direction in relation to the shaft 1. In this case, techniques known per se can be used and so these gear means 21 are not explained in further detail.

An outer sleeve 22 is mounted on the shaft 1 for displacement in longitudinal direction and this sleeve consists of an electrically insulating material. In the advanced state it covers the flexible wall sections 17 of the shaft 1 and thus holds their inwardly projecting ends 16 in the circumferential groove 15 of the insertion nipple 10; as a result, the holder 9 is held in the shaft 1 so as to be non-displaceable in axial direction. To release this connection it is sufficient for the outer sleeve 22 to be pushed back so that the wall sections 17 can spring outwards; their ends 16 thereby exit from the circumferential groove 15 and the holder can then be withdrawn from the shaft 1.

As a result of the use of an electrically insulating material, the outer sleeve 22 covers, in addition, the entire shaft 1 and the cylindrical section 11 of the holder 9 when the holder is inserted.

A broad circumferential groove 23 is formed in the insertion nipple 10 and this groove is limited laterally by respective steps 24. The step is designed in cross section to be undercut by a boundary surface 25 extending at an angle. In addition, a narrow circumferential groove 27 with an essentially triangular cross-sectional surface area is worked into the base 26 of the circumferential groove 23.

The circumferential groove 23 accommodates a plastic sheath 28 which fills it completely and supports longitudinal ribs 29 protruding radially beyond the outer surface of the insertion nipple 10. During the insertion of the insertion nipple 10 into the shaft 1, these longitudinal ribs slide into the longitudinal cuts 18 between the wall sections 17 and form a means for securing the holder 9 against rotation. In the area located between the longitudinal ribs 29, the plastic sheath 28 adjoins the circumferential surface of the insertion nipple 10 in the areas located next to the circumferential groove 23 in a stepless manner.

The plastic sheath 28 can, for example, be applied by spraying around the holder in the area of the circumferential groove 23. The plastic material applied in this way engages beneath the step 24 forming an undercut so that in the area of the edge of the plastic sheath 28 a positive connection is formed between plastic sheath 28, on the one hand, and insertion nipple 10, on the other hand, and this connection prevents the plastic sheath 28 from being able to lift away from the base 26 of the circumferential groove 23 in a radial direction. As a result of the material of the plastic sheath 28 engaging in the circumferential groove 27, an axial securing is achieved, in addition.

Figure 3:
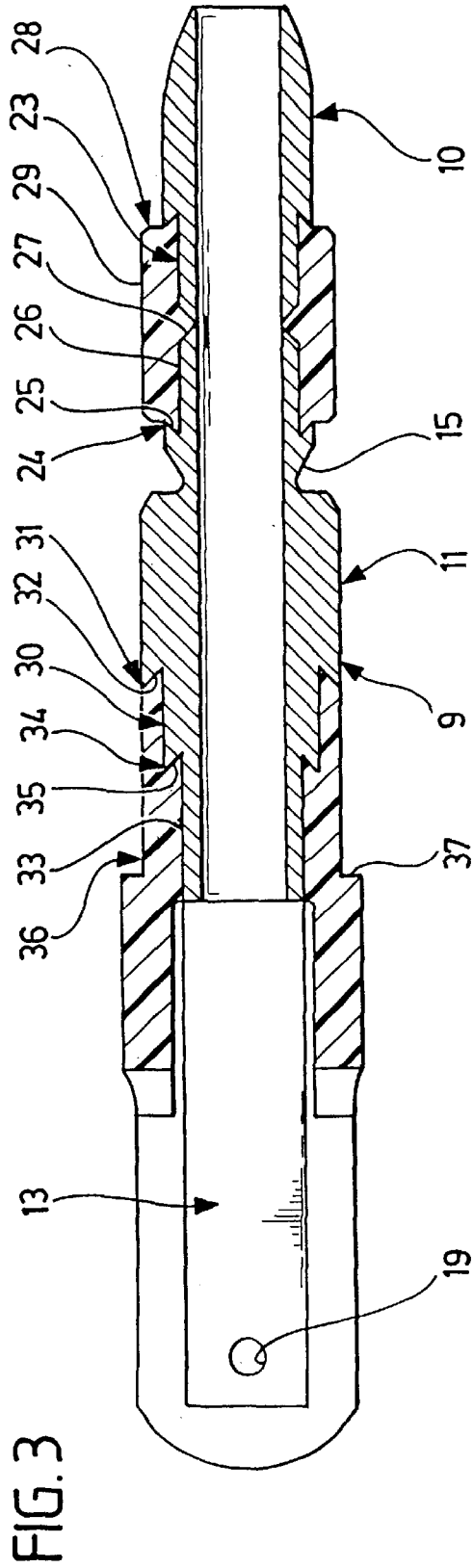
FIG. 3 a longitudinal sectional view of the holder of FIG. 2.
Figure 4:
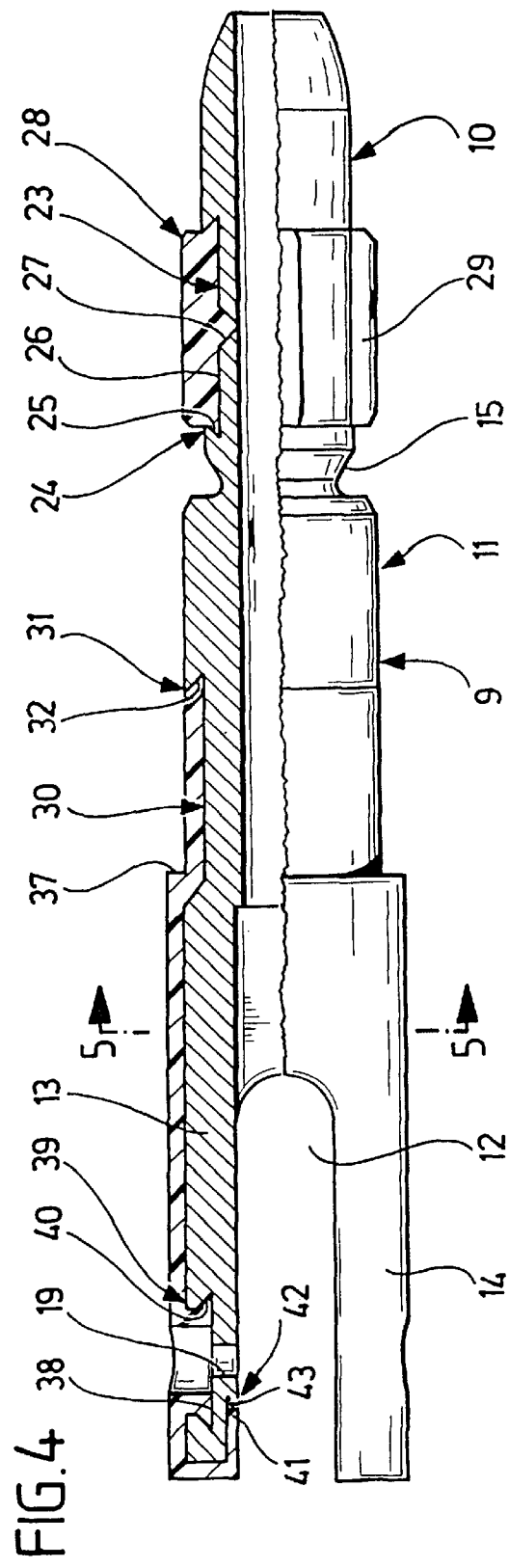
FIG. 4 a side view of the holder of FIG. 3 in a position turned through 90° with partially cutaway areas and FIG. 5 a sectional view along line 5—5 in FIG. 4.

A circumferential groove 30, which extends approximately from the center of the cylindrical section 11 as far as the start of the longitudinal arms 13, 14, is likewise located in the cylindrical section 11. This circumferential groove 30 is limited at its distal end by a step 31 which is likewise undercut and has an inclined boundary surface 32. A further groove 33 extending in circumferential direction is let into this circumferential groove 30 over part of the circumference and this groove 33 forms a recess in the base of the circumferential groove 30 and is likewise limited by an undercut step 34 with an inclined boundary surface 35 (FIG. 3).

The circumferential groove 30 and the groove 33 are completely filled by an additional plastic sheath 36 which merges in the area of the step 31 in a stepless manner into the circumferential surface of the cylindrical section 11. In the area of transition between the cylindrical section 11 and the longitudinal arms 13, 14, this plastic sheath 36 forms a step 37 which projects radially outwards and forms a stop for the outer sleeve 22.

The plastic sheath 36 continues on the outer side of the longitudinal arms 13 and 14 and surrounds these on the upper side, on the outer side and on the underside as well as at the end side and at the distal end of the inner side.

In the area of the openings 19, the longitudinal arms 13 and 14 have cylindrical recesses 38, the outer edge of which forms an undercut step 39 with an inclined boundary surface 40. The plastic sheath 36 engages in this recess 38 but leaves the central area of the recess 38 free so that the opening 19 remains accessible from the outside.

The edge 41 of the plastic sheath 36 located on the inner side of the longitudinal arms engages beneath a likewise undercut step 42 with an inclined boundary surface 43 which extends between the distal end of the longitudinal arms 13, 14, on the one hand, and the opening 19, on the other hand, transversely to the longitudinal direction of the longitudinal arms 13, 14.

It is ensured in this way that the plastic sheath is held positively on the holder 9 in the area of the steps 31, 34 as well as 39 and 42 and is secured against any separation.

A similar securing results on the upper side and on the underside of the longitudinal arms 13 and 14; these have towards their inner side longitudinal grooves 44, which extend parallel to the longitudinal direction of the longitudinal arms 13, 14, are open towards the inner side and the side walls 45 of which are undercut, namely by an inclined design of the boundary surfaces 45. These longitudinal grooves 44 with the undercut boundary surfaces 45 are also filled by the material of the plastic sheath 36 and thereby positively secured against any separation.

The plastic sheath 36 has a completely closed design in the area adjacent to the cylindrical section 11, as illustrated in FIG. 5. This applies for the area of the longitudinal arms 13 and 14, into which the receiving space 12 does not extend. In the area of the receiving space 12, on the other hand, this remains laterally recessed in the plastic sheath 36 so that tools dipping into the receiving space 12 can be pivoted sidewards out of the receiving space 12.

What is claimed is:

1. A surgical tubular-shafted instrument adapted for sterilization, said instrument having:
    a shaft,
    at least one surgical tool being arranged on a holder at the distal end of said shaft, said holder being secured in position on the shaft,
    projections on the holder formed by undercuts of steps in the holder,
    a plastic sheath partially covering the holder, and
    a backwardly tapering cavity of each undercut, wherein:
    the plastic sheath engages beneath said projections on the holder to electrically insulate said holder in a manner that is positively secured against separation during use and sterilization;
    said steps limit a lower-lying area of the holder covered by the plastic sheath; and
    each backwardly tapering cavity is completely filled by the material of the plastic sheath.

2. Instrument as defined in claim 1, wherein each undercut is formed by a boundary surface of the step extending at an angle to the height of the step.

3. Instrument as defined in claim 1, wherein the plastic sheath adjoins non-sheathed, adjacent areas of the holder in a stepless manner.

4. Instrument as defined in claim 1, wherein the material of the plastic sheath is polyether ether ketone (PEEK).

5. Instrument as defined in claim 1, wherein the material of the plastic sheath is liquid crystal polymer (LCP).

6. A surgical tubular-shafted instrument adapted for sterilization, said instrument having:

a shaft, at least one surgical tool being arranged on a holder at the distal end of said shaft, said holder being secured in position on the shaft, projections on the holder formed by undercuts of steps in the holder, and a plastic sheath partially covering the holder, wherein:

the plastic sheath engages beneath said projections on the holder to electrically insulate said holder in a manner that is positively secured against separation during use and sterilization;

said steps limit a lower-lying area of the holder covered by the plastic sheath; and each undercut is formed by a boundary surface of the step extending at an angle to the height of the step.

7. Instrument as defined in claim 6, wherein the plastic sheath adjoins non-sheathed, adjacent areas of the holder in a stepless manner.

8. Instrument as defined in claim 6, wherein the material of the plastic sheath is polyether ether ketone (PEEK).

9. Instrument as defined in claim 6, wherein the material of the plastic sheath is liquid crystal polymer (LCP).

* * * * *